（12) United States Patent
Meng et al.

(10) Patent No.: US 8,217,670 B2
(45) Date of Patent: Jul. 10, 2012

(54) LABEL-FREE SENSOR (75) Inventors: Hsin-Fei Meng, Hsinchu (TW);
Sheng-Fu Hong, Hsinchu (TW);
Yu-Chiang Chao, Hsinchu (TW);
Chien-Cheng Liu, Hsinchu (TW);
Wen-Hsing Liu, Hsinchu (TW);
Cheng-Chung Chang, Hsinchu (TW);
Jan-Hao Li, Hsinchu (TW); Ming-Zhi Dai, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 497 days.

(21) Appl. No.: 12/500,689

(22) Filed: Jul. 10, 2009

(65) Prior Publication Data
US 2010/0237885 A1 Sep. 23, 2010

(30) Foreign Application Priority Data
Mar. 17, 2009 (TW) ................................ 98108545 A (51) Int. Cl.
*G01R 27/08* (2006.01)
(52) U.S. Cl. ........................................ 324/717; 324/713
(58) Field of Classification Search .................. 324/717,
324/715, 713, 691, 649, 600; 435/6.19, 6.11,
435/6.1, 4; 422/82.03, 82.01, 68.1, 50
See application file for complete search history.

(56) References Cited

U.S. PATENT DOCUMENTS

| | | | | |
|---|---|---|---|---|
| 6,365,825 B1 * | 4/2002 | Hayashi et al. | ............... | 136/243 |
| 6,734,090 B2 * | 5/2004 | Agarwala et al. | ............. | 438/598 |
| 7,509,860 B2 * | 3/2009 | Lee et al. | ........................ | 73/579 |
| 2006/0121501 A1 * | 6/2006 | Jabs et al. | ......................... | 435/6 |
| 2007/0007538 A1 * | 1/2007 | Ono et al. | ........................ | 257/79 |
| 2007/0259359 A1 * | 11/2007 | Briman et al. | ..................... | 435/6 |
| 2010/0084634 A1 * | 4/2010 | Gamo et al. | .................... | 257/40 |
| 2010/0294659 A1 * | 11/2010 | Green | .......................... | 204/400 |

OTHER PUBLICATIONS

Kuzmych et al., Nanotechnology, 18:1-7 (2007).
Cui et al., Science, 293:1289-1292 (2001).
Kam et al., J. Am. Chem. Soc., 126:6850-6851 (2004).
Star et al., PNAS, 103(4):921-926 (2006).

* cited by examiner

*Primary Examiner* — Hoai-An D Nguyen
(74) *Attorney, Agent, or Firm* — Edwards Wildman Palmer LLP; Peter F. Corless (57) ABSTRACT

The invention provides a label-free sensor that includes a substrate, a first electrode formed on the substrate, a second electrode formed on the substrate and spaced away from the first electrode, and a semiconductor layer formed on the substrate and being in contact with the first electrode and the second electrode. The semiconductor layer has a plurality of probe groups bonded to the semiconductor layer by functionalization, for sensing a coupling-specific substance having bonding specificity with the probe groups. The semiconductor layer is bonded with the probe groups, and the detection of detected object is performed in an instant, quick, rapid, and sensitive manner by measuring variation in electric current, avoiding the use of fluorescent reading equipment for reading fluorescent signals.

18 Claims, 8 Drawing Sheets

LABEL-FREE SENSOR

1. FIELD OF INVENTION

The present invention relates to a sensor, and more particularly, to a label-free sensor for biological applications.

2. BACKGROUND OF THE INVENTION

With rapid progress in biotechnology and medical treatment, the molecular biological detection has become a major subject of investigation. The molecular biological detection utilizes specific molecular markers or specific activity of specific molecules to distinguish different molecules by selective detection. The molecular biological detection, which is for sensing the presence of trace amount of protein, nucleic acid, or compounds in organism or environment such as early diagnoses of diseases and detection of environmental factors such as environmental hormones in high-specificity and high-sensitivity manners, is particularly important in different fields including medical science, life science, food detection, environmental sanitation, etc. The developing of high-sensitivity, instant, accurate, high-throughput detections has currently become a major trend of investigation.

It is therefore a challenging and interdiscipline-intergrated subject to develop a new detection technology by utilizing the existing maturated or developing technologies effectively. In recent years, there are disclosed many biosensors or sensing methods, which can be classified into sensing methods of labeling the target substances with fluorescence or luminescent markers and the high-sensitivity methods such as surface plasma resonance (SPR), Quartz crystal microbalance (QCM), carbon nanotube field-effect transistor (CNT FET) and nanowire FET for detecting the bonding to the target substances. The target substances with weight range from nanogram to pictogram can be sensed by means of the above-mentioned sensing methods or sensors.

The current nano-sized biosensors are mostly made of silicon nanowires or nanotubes.

As exemplified by the silicon nanowire, the surface of silicon is oxidized easily to form the native oxide layer. Accordingly, it is much easier to sense the presence of the electrified molecules such as proteins. However, it is not easy to manufacture the silicon nanowire, and the equipment required for manufacture is extremely expensive. O. Kuzmych et al., Nano technology 18, 375502 (2007) discloses a silicon nanowire sensor. The U.S. Pat. Nos. 7,129,554 and 6,870,235 both disclose a sensor that adopts silicon nanowire as field-effect transistor on which probe molecules are coupled for selective detection. By means of the structure of silicon nanowire, the above-mentioned sensors provide shorter sensing time while they still cause shortcomings including complexity or yield lower than 50% in manufacture.

As exemplified by the nanotube, it can be manufactured with high throughput, but it is not easy to obtain the nanotube with complete semiconductor properties by purification. In addition, it is very difficult to functionalize the nanotube for the researchers who have no chemistry background. The U.S. Pat. No. 7,318,908 discloses nanotube sensor arrays that adopt the nanotubes as field-effect transistors on which probe molecules are coupled for selective detection. However, the probe molecules are likely separated from the nanotubes according to the method disclosed in this reference. In addition, the Y. Chi et al. Science 293,1289 (2001) and N. W. S. Kam et al., J. Am. Chem. Soc. 126, 6850-6851 2004) also disclose nanotube sensors.

Star A et al., Proc. Natl acad. Sci. USA 103,921 (2006) discloses label-free detection of DNA hybridization using carbon nanotube network field-effect transistors. However, the use of specific fluorescent reading equipment is still unavoidable for reading fluorescent signals, causing complexity to detection procedure.

Accordingly, there still exists a need to develop a nanosensor capable of reading the molecular signals easily and improving the above-mentioned conventional problems.

SUMMARY OF THE INVENTION

In view of the foregoing shortcomings in the conventional technologies, it is therefore an object of the present invention to provide a label-free sensor to facilitate signal reading.

In order to achieve the above and other objects, the present invention discloses a label-free sensor, which comprises a substrate, a first electrode formed on the substrate, a second electrode formed on the substrate and spaced away from the first electrode, and a semiconductor layer formed on the substrate and in contact with the first electrode and the second electrode, wherein the semiconductor layer has a plurality of probe groups, which are bonded to the semiconductor layer by functionalization, for sensing a substance, which has bonding specificity with the probe groups.

Specifically, the semiconductor layer of the label-free sensor of the present invention is sandwiched between the substrate and the first and second electrodes. In other words, the first electrode and the second electrode are formed on the semiconductor layer such that the semiconductor layer is sandwiched between the substrate and the first and second electrodes. Alternatively, the first electrode and the second electrode are formed on the substrate in contact with the substrate. In addition, partial portion of the semiconductor layer is formed on the first electrode and the second electrode such that the first electrode and the second electrode are sandwiched between the substrate and the semiconductor layer, wherein the second electrode is spaced away from the first electrode by the semiconductor layer.

In one aspect, the semiconductor layer is of a porous metal oxide. Preferably, the porous metal oxide is selected from the group consisting of zinc oxide ($ZnO_x$), titanium oxide ($TiO_x$), indium oxide ($InO_x$), and a combination thereof.

In another aspect, the semiconductor layer is, for example, of organic polymer semiconductor, but not limited to:

Preferably, the semiconductor layer is an organic polymer semiconductor with porous configuration. In addition, the organic polymer is deposited in the form of silk by, for example, electrospinning method. The silk-shaped organic polymers are stacked on one another to form the porous semiconductor with porous configuration.

The semiconductor layer is functionalized with chemical groups or biomolecules to be provided with probe groups. The probe groups are chemical groups selected from the group consisting of —OH, —CHO, —COOH, —SO$_3$H, —CN, —NH$_2$, —SH, —COSH, —COOR, and halide. Alternatively, the probe groups are biomolecules selected from the group consisting of nucleic acid, antibody, antigen, carbohydrate, protein, amino acid, and enzyme. The probe groups are such as biotins.

In a further application, the biomolecule is able to tightly bond the probe group to the porous semiconductor. Alternatively, the biomolecule itself is a probe group to be specifically boned to a specific molecule. In a preferred embodiment, the biomolecules are selected from the group consisting of nucleic acid, antibody, antigen, carbohydrate, protein, amino acid, and enzyme.

As exemplified by biotin, the biotin can be specifically boned to the acceptor such as avidin. Therefore, the sensor device is adaptable for sensing the presence of avidin. In addition, the sensor of the present invention has no response to other substances, which has no specific bonding to the avidin. Accordingly, the purpose of specific sensing is achieved.

In one embodiment, the sensor of the present invention comprises a substrate, two metal electrodes, and a porous semiconductor layer, wherein the porous semiconductor layer may be located on the substrate on which the metal electrodes are formed to form a bottom contact structure. Alternatively, the porous semiconductor layer may be formed on the substrate and then the metal electrodes are formed thereon to form a top contact structure.

In the embodiment, the porous polymer semiconductor in the sensor of the present invention is supplied with probe groups by functionalizing the organic polymer, and then the electrospinning method is performed to form the porous silk-shape stacked configuration for thereby forming the porous organic polymer semiconductor layer. Alternatively, the organic polymer is provided with the silk-shape stacked configuration, and then the functionalization step is performed to be bonded with probe groups.

The present invention further provides a sensing method, which comprises the steps of: applying a bias voltage to the first electrode and the second electrode of the label-free sensor of the present invention for generating an electric current; contacting a detected object with the probe groups bonded to the semiconductor layer of the label-free sensor; and measuring a variation in the electric current generated by the label-free sensor so as to determine whether a coupling-specific substance exists in the detected object.

In one preferred embodiment, the semiconductor layer is of a metal oxide. Preferably, the semiconductor layer is of porous metal oxide or porous organic polymer semiconductor. The porous organic polymer semiconductor is functionalized with chemical groups or bio-molecules.

In the embodiment, the detected object and the sensor are in contact with each other in a liquid. The sensor is disposed in the liquid, and a bias voltage is applied to generate an electric current. After the electric current is stabilized, the detected objected is then disposed in the liquid. If the contact of the detected object and the sensor causes the variation in electricity, then it is concluded that a coupling-specific substance, which is specifically bonded to the probe groups, exists in the detected object.

In one preferred embodiment, the detected object is a gaseous or gas-generating object. For instance, a bias voltage is applied to the sensor to generate an electric current. After the electric current is stabilized, the gaseous detected object is introduced to contact the detected object with the sensor. The variation in electricity is then measured. If the contact between the detected object and the sensor causes the variation in the electricity, then it is concluded that a specific substance, which is specifically bonded to the probe groups, exists in the detected object.

The present invention further provides a sensing system, which comprises the sensor of the present invention, a voltage supply device electrically connected to the first and second electrodes for applying a bias voltage to the sensor, and an electricity measuring device electrically connected to the sensor for measuring a variation in electricity.

In a preferred embodiment, the variation in electricity is a variation in an electric current.

The sensor of the present invention advantageously provides with the instant, quick, rapid, and sensitive detection. The sensor of the present invention has no need to label the detected object, and therefore can improve the unavoidable process for operating the conventional sensor. In addition, the detection process of the sensor of the present invention can be performed merely by measuring the variation in the electric current without the use of large-sized, expensive detection equipment, thereby achieving the purposes of cost reducing and high-throughput screening.

DETAILED DESCRIPTION OF THE PREFERRED EMBODIMENTS

Some of embodiments are herein described in detail to explain the present invention, and numerous advantages and effects will become readily apparent to person ordinarily skilled in the art once the disclosure is fully appreciated. It should be noted that the present invention may be implemented with various embodiments.

PREPARATION EXAMPLE 1 FOR SEMICONDUCTOR DEVICE (1) Preparation of Metal-Oxide-Semiconductor (MOS) Device A solvent such as 2-propanol or anhydrous ethanol is utilized to prepare a solution of zinc acetate (purchased from Sigma Aldrich company) with a concentration of 0.5M to 1.0M, and ethanolamine is then added thereinto, wherein the zinc acetate and the ethanolamine are in a molar ratio of 1:1 and this solution may be undoped or doped with aluminum nitrate and the zinc acetate with a molar ratio of 1:99 to 5:95. The zinc acetate solution (or called as zinc oxide precursor) is sprayed on a glass substrate by spin-on-glass method, and the solvent is then removed by baking at 200° C. Thereafter, a post-anneal treatment is performed in a furnace at a temperature range of 400 to 600° C. depending on the heat resistance of the substrate so as to form the zinc oxide semiconductor layer.

Figure 1A:
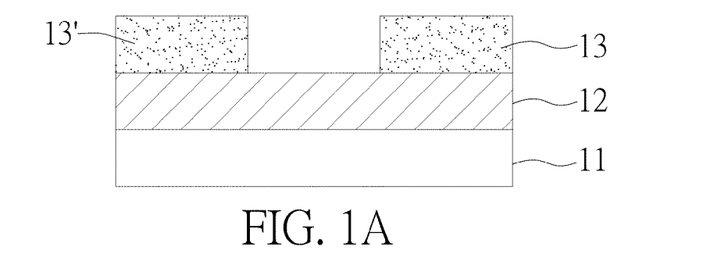
FIG. 1A and FIG. 1B are schematic diagrams illustrating the structures of metal oxide semiconductors respectively.

A metal electrode such as aluminum (Al) or titanium (Ti) is evaporated on the zinc oxide semiconductor layer by using a metal mask so as to form the metal oxide semiconductor device with a top contact structure, wherein the metal oxide semiconductor device comprises a glass substrate 11, a semiconductor layer 12 formed on the glass substrate 11, a first electrode 13, and a second electrode 13', as shown in FIG. 1A.

Figure 1B:
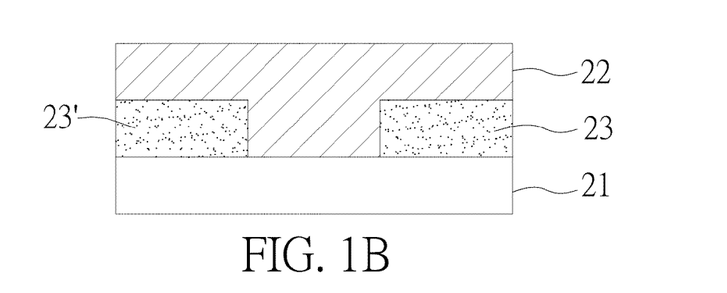
Figure 2A:
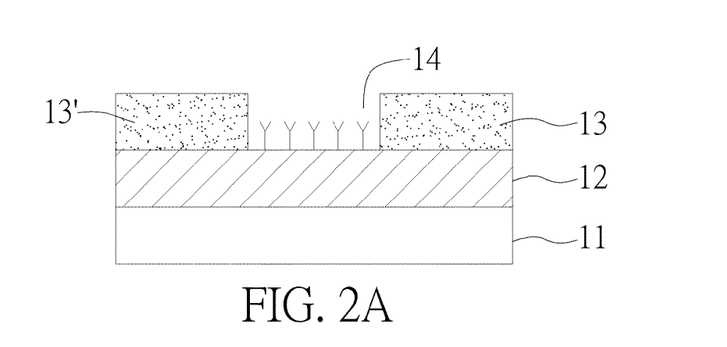
FIG. 2A and FIG. 2B are schematic diagrams illustrating the functionalized structures of metal oxide semiconductors respectively.
Figure 2B:
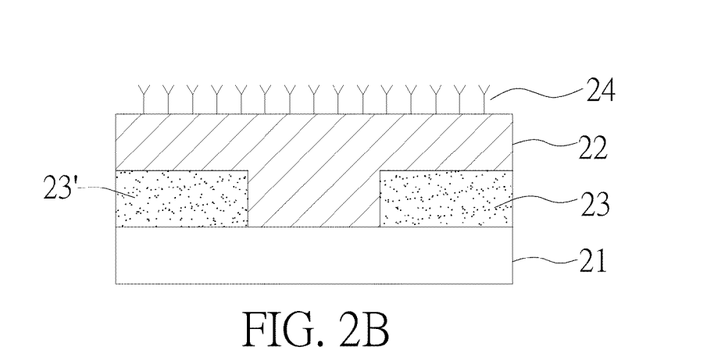

Alternatively, before the zinc acetate solution is sprayed, the photolithography method or the metal mask method is utilized for forming the metal electrode on the glass substrate while the remaining steps are identical to that described above so as to form the metal oxide semiconductor device with a bottom contact structure, wherein the metal oxide semiconductor device comprises a glass substrate 21, a semiconductor layer 22, a first electrode 23, and a second electrode 23', as shown in the FIG. 1B.

(2) Preparation of Metal-Oxide-Semiconductor (MOS) Device

A solvent such as 2-propanol or anhydrous ethanol is utilized to prepare a solution of zinc acetate (purchased from Sigma Aldrich Company) with a concentration of 0.5M to 1.0M, and ethanolamine is then added thereinto, wherein the zinc acetate and the ethanolamine are in a molar ratio of 1:1 and this solution may be undoped or doped with aluminum nitrate and the zinc acetate with a molar ratio of 1:99 to 5:95.

Figure 3A:
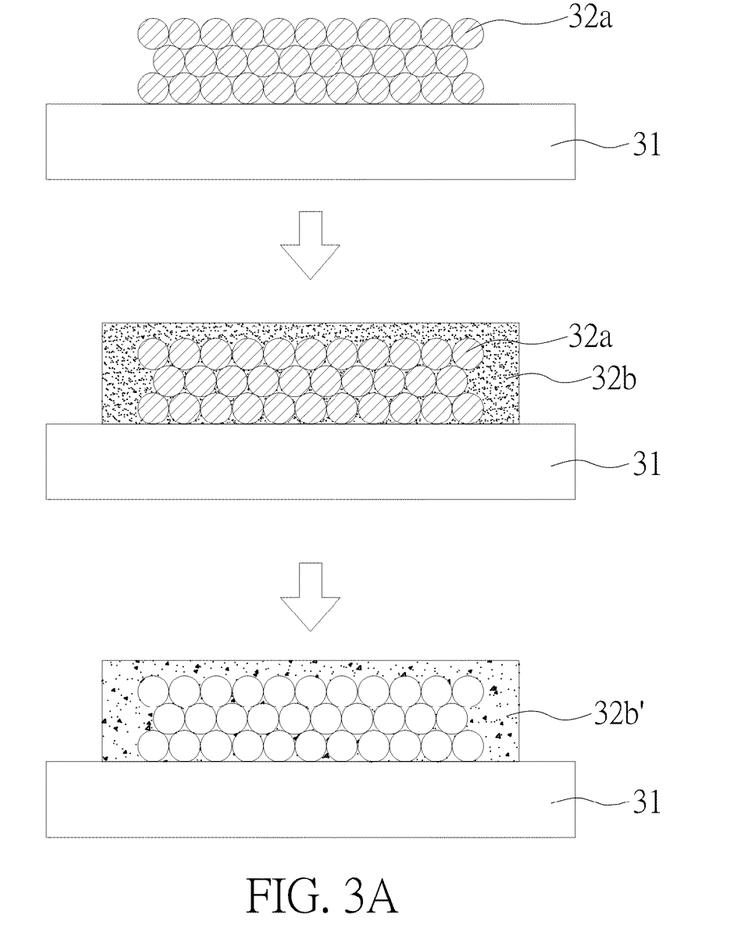
FIG. 3A is a diagram showing the process of manufacturing porous metal oxide semiconductor layer.
Figure 3B:
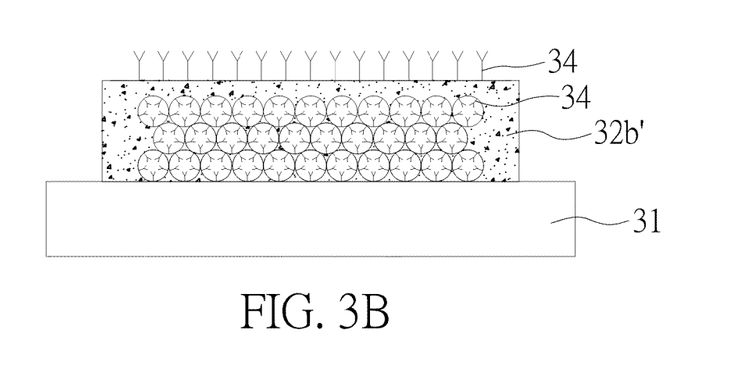
FIG. 3B is a schematic diagram showing the functionalized structure of porous metal oxide semiconductor layer.

As the process shown in FIG. 3A, polystyrene spheres (purchased from Fluka Company) is sprayed on a glass substrate 31 by the spin-on-glass method, and baked at 115° C. for about 5 minutes such that the polystyrene spheres 32a will be self-stacked on the substrate 31. Then, the zinc acetate solution (or called as zinc oxide precursor) is sprayed on the glass substrate with the polystyrene spheres 32a stacked thereon by the spin-on-glass method for thereby forming the zinc oxide precursor layer 32b. Thereafter, the solvent is removed by baking at 200° C., and a post-anneal treatment is performed in a furnace at a temperature range of 400 to 600° C. depending on the heat resistance of the substrate. Under such a high temperature, the zinc oxide precursor will be transformed into the zinc oxide and the polystyrene spheres will be vaporized to form voids in the zinc oxide semiconductor layer such that the porous zinc oxide semiconductor layer 32b' is thus formed.

A metal electrode such as aluminum (Al) or titanium (Ti) is evaporated on the zinc oxide semiconductor layer by using a metal mask so as to form the metal oxide semiconductor device with a top contact structure.

Alternatively, before the step of forming the porous zinc oxide semiconductor layer, the photolithography method or the metal mask method is utilized for forming the metal electrode on the glass substrate while the remaining steps are identical to that described above so as to form the porous metal oxide semiconductor device with a bottom contact structure.

(3) Preparation of Organic Polymer Semiconductor Device

An organic polymer solution with a concentration of 0.051M is prepared by using poly[3-(potassium-6-hexanoate)thiophene-2,5-diyl], purchased from Rieke Metal Company. This organic solution is then sprayed on a glass substrate by the spin-on-glass method, and baked to remove solvent at 200° C. for forming the organic polymer semiconductor layer.

A metal electrode such as aluminum (Al) or titanium (Ti) is evaporated on the zinc oxide semiconductor layer by using a metal mask so as to form the organic polymer semiconductor device with a top contact structure.

Alternatively, before the organic solution is sprayed, the photolithography method or the metal mask method is utilized for forming the metal electrode on the glass substrate while the remaining steps are identical to that described above so as to form the organic polymer semiconductor device with a bottom contact structure.

(4) Preparation of Porous Organic Polymer Semiconductor Device

Figure 4A:
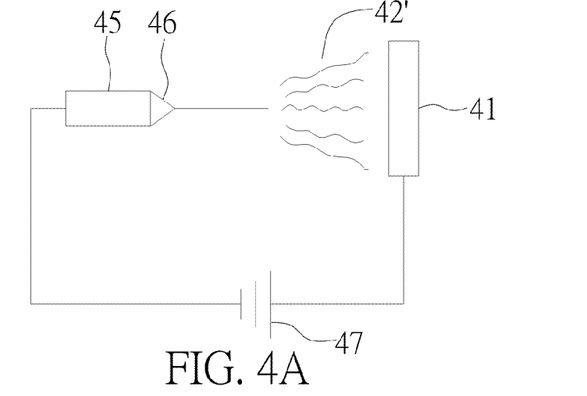
FIG. 4A is a schematic diagram showing the process of manufacturing porous organic polymer semiconductor layer.

In the preparation process shown in FIG. 4A, the porous organic polymer is prepared by using electrospinning method.

Figure 4B:
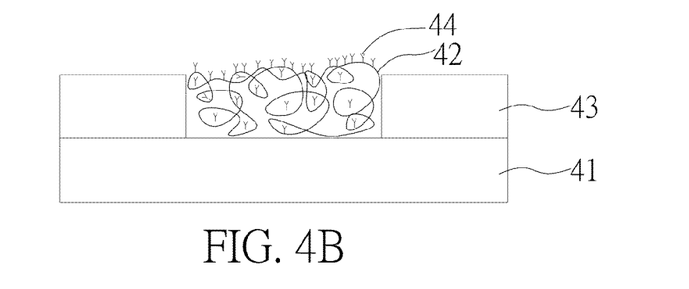
FIG. 4B is a schematic diagram showing the functionalized structure of porous organic polymer semiconductor layer.
Figure 4C:
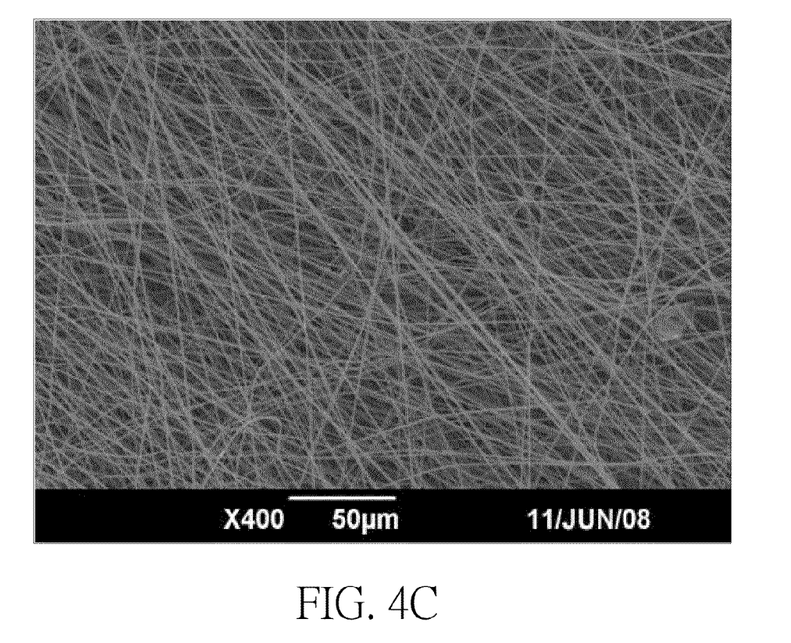
FIG. 4C is a SEM diagram showing the porous configuration formed by electrospinning method.

The poly[3-(potassium-6-hexanoate)thiophene-2,5-diyl] solution is disposed into a syringe 45, and ejected out of a metal syringe needle 46, wherein high voltage (10 kV~20 kV) is applied between the metal syringe needle 46 and syringe 45 by using a high voltage supply device 47 such that the organic polymer solution 42', which is ejected out, will be deposited in the form of silk on a glass substrate 41 on which a metal electrode 43 is formed for thereby forming the porous organic polymer semiconductor layer 42, as shown in FIG. 4B. As shown in FIG. 4C, the porous configuration is formed due to the voids generated by stacking of the organic polymer silks.

PREPARATION EXAMPLE 2 FOR FUNCTIONALIZATION (1) Functionalization of Semiconductor by Hemin A solvent such as dimethylsulfoxide (DMSO) is utilized to prepare a solution of hemin (purchased from Sigma Aldrich Company) with a concentration of 0.5M to 1.0M, and the semiconductor device of the preparation example 1 is dipped into the hemin solution for at least 5 to 60 minutes. Thereafter, the DMSO is utilized to clean the surface of the semiconductor device and remove the hemin, which is not bonded to the semiconductor device, for thereby obtaining a hemin-functionalized sensor device, which is adaptable for sensing the presence of nitric oxide (NO).

(2) Functionalization of Semiconductor by Biotin

A phosphate buffer solution (PBS) with a pH of about 7.0 and a concentration of 0.01M is adopted as a solvent to prepare a solution of biotin (purchased from Sigma Aldrich Company) with a concentration of 2 mM, and the semiconductor device of the preparation example 1 is dipped into the biotin solution overnight. Thereafter, the PBS is applied to clean the surface of the semiconductor device and remove the biotin, which is not bonded to the semiconductor device, for thereby obtaining a biotin-functionalized sensor device adaptable for sensing the presence of avidin.

Additionally, with respect to the functionalization of organic polymer semiconductor, a phosphate buffer solution (PBS) with a pH of about 7.0 and a concentration of 0.01M is adopted as a solvent to prepare a solution of amine-$PEO_2$-biotin (purchased from Pierce Biotechnology Company) with a concentration of 1 mM, and the organic polymer semiconductor device of the preparation example 1 is dipped into the amine-$PEO_2$-biotin solution so as to enable the —COOH group contained in the terminal of the organic polymer and the —$NH_2$ group of amine-$PEO_2$-biotin to generate chemical reaction for forming covalence bonding therebetween. After dipping overnight of the organic polymer semiconductor device, the PBS is applied to clean the surface of the semiconductor device and remove the biotin, which is not bonded to the semiconductor device, for thereby obtaining a biotin-functionalized sensor device adaptable for sensing the presence of avidin.

(3) Functionalization of Semiconductor by 3,4-diaminobenzoic Acid

A phosphate buffer solution (PBS) with a pH of about 7.0 and a concentration of 0.01M is adopted as a solvent to prepare a solution of 3,4-diaminobenzoic acid (purchased from Sigma Aldrich Company) with a concentration of 2 mM, and the semiconductor device of the preparation example 1 is dipped into the 3,4-diaminobenzoic acid solution overnight. Thereafter, the PBS is applied to clean the surface of the semiconductor device and remove the 3,4-diaminobenzoic acid, which is not bonded to the semiconductor device, for thereby obtaining a 3,4-diaminobenzoic acid-functionalized sensor device adaptable for sensing the presence of nitric oxide (NO).

The schematic diagrams of functionalized semiconductor are shown in FIGS. 2A, 2B, 3B, and 4B respectively, wherein the symbols 14, 24, 34, and 44 represent the probe groups of the semiconductor layers.

Embodiment 1

The semiconductor device of the preparation example 1 (1) is functionalized by, for example, using the steps described in the preparation example 2 (2) so as to obtain the biotin-functionalized zinc oxide semiconductor sensor device (hereinafter abbreviated as biotin-zinc oxide sensor device)

Figure 5:
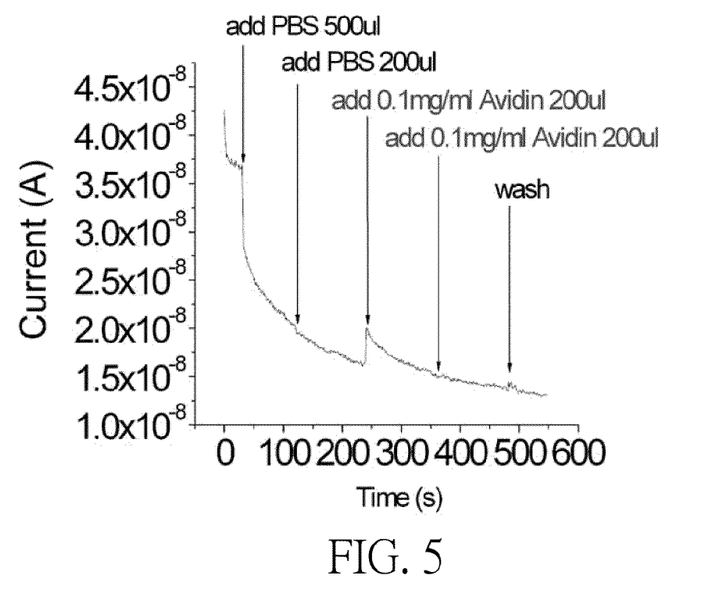
FIG. 5 is diagram showing variation in electric current of biotin-zinc oxide sensor device.

The biotin-zinc oxide sensor device is applied with a voltage, and disposed in a PBS buffer solution with a pH of 7.0 and a concentration of 0.01M, as shown in FIG. 5. When the biotin-zinc oxide sensor device initially touches 500 µl of the PBS buffer solution, the electric current is dropped significantly. When additional 200 µl of the PBS buffer solution is further added, the electric current will not be varied significantly by the addition of the PBS buffer solution. Therefore, it is concluded that the variation in electric current during the addition of the PBS buffer solution is not caused by the PBS buffer solution itself.

Thereafter, 200 µl of 0.1 mg/ml avidin with coupling-specific substance (purchased from Sigma Aldrich Company) is added to the PBS buffer solution that contains the biotin-zinc oxide sensor device so as to generate an obvious variation in electric current immediately due to the specific bonding between the avidin and biotin-functionalized semiconductor layer, wherein the electric current is varied by the variation in the carrier transportation of the zinc oxide semiconductor layer, which is affected by the charges of the avidin. As a result, it is verified that the sensor of the present invention, which has no need to label substrate, is capable of sensing the presence of coupling-specific substance by the variation in the electric current.

Embodiment 2

The semiconductor device of the preparation example 1 (1) is functionalized by, for example, using the steps described in the preparation example 2 (3) so as to obtain the 3,4-diaminobenzoic acid-functionalized zinc oxide semiconductor sensor device (hereinafter abbreviated as aminobenzoic-zinc oxide sensor device)

Figure 6:
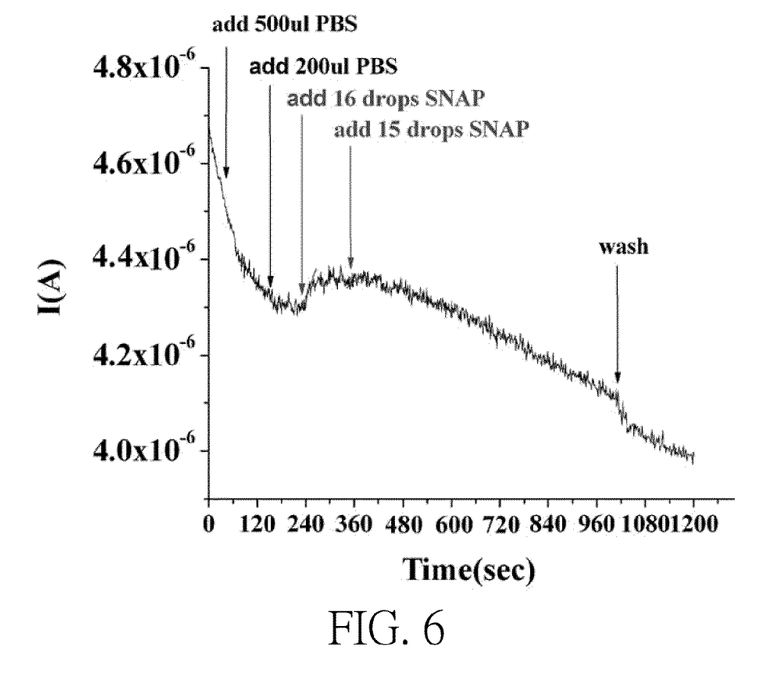
FIG. 6 is diagram showing variation in electric current of aminobenzoic-zinc oxide sensor device.

The aminobenzoic-zinc oxide sensor device is applied with a voltage, and disposed in a PBS buffer solution with a pH of 7.0 and a concentration of 0.01M, as shown in FIG. 6. When the aminobenzoic-zinc oxide sensor device initially touches 500 µl of the PBS buffer solution, the electric current is dropped significantly. When additional 200 µl of the PBS buffer solution is further added, the electric current will not be varied significantly by the addition of the PBS buffer solution. Therefore, it is concluded that the variation in electric current during the addition of the PBS buffer solution is not caused by the PBS buffer solution itself.

16 drops of NO donor SNAP (S-Nitroso-N-acetyl-DL-penicillamine, purchased from Sigma Aldrich Company with a concentration of 0.5M) are added to the PBS buffer solution that contains the aminobenzoic-zinc oxide sensor device, wherein an obvious variation in electric current will be generated immediately because the SNAP is a substrate donor of the 3,4-diaminobenzoic acid. Therefore, it is verified that the sensor of the present invention, which has no need to label acceptor, is capable of sensing the presence of coupling-specific substance by the variation in the electric current.

Embodiment 3

The semiconductor device of the preparation example 1 (1) is functionalized by, for example, using the steps described in the preparation example 2 (1) so as to obtain the hemin-functionalized zinc oxide semiconductor sensor device (hereinafter abbreviated as hemin-zinc oxide sensor device).

Figure 7:
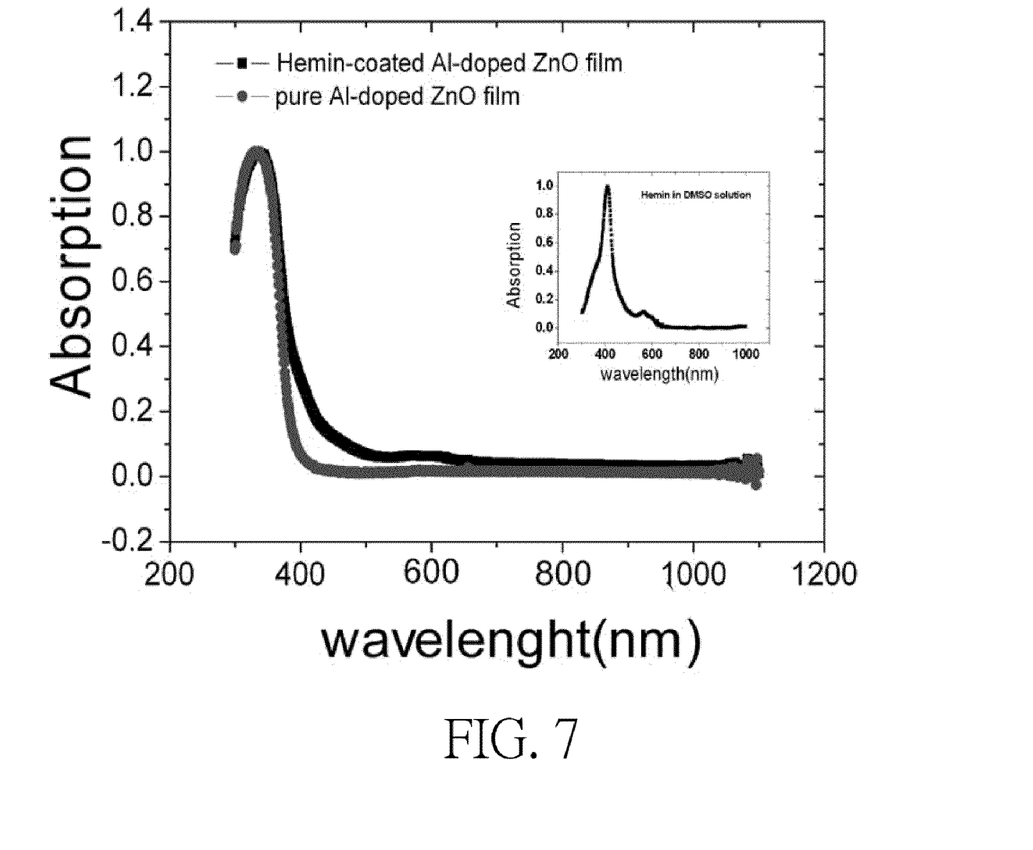
FIG. 7 is diagram showing absorption spectrums of hemin-zinc oxide sensor device and hemin dissolved in DMSO solution, wherein -■- represents hemin-functionalized zinc oxide and -●- represents comparison group (un-functionalized zinc oxide)

The absorption spectrum of the hemin-zinc oxide sensor device prepared by the above-mentioned steps is obtained, and the purified hemin dissolved in the DMSO solution and the un-functionalized zinc oxide semiconductor device are adopted as comparison groups. The results are shown in FIG. 7, within the visible wavelength range of 400 nm~600 nm, the hemin-zinc oxide sensor device has absorption phenomenon, which is identical to that of the hemin dissolved in the DMSO solution. It is verified that the sensor of the present invention is actually functionalized with hemin on the zinc oxide.

The un-functionalized zinc oxide semiconductor device and the hemin-zinc oxide sensor device are disposed respectively into the environment fulfilled with nitrogen gas, and the devices are applied with a voltage. Thereafter, the NO gas is supplied into the environment that is fulfilled with nitrogen gas. In addition, the variations in the electric currents of the sensor device when the concentration of NO gas is adjusted and when the supply of NO gas is turned on and turned off are shown in FIGS. 8A and 8B respectively.

Figure 8A:
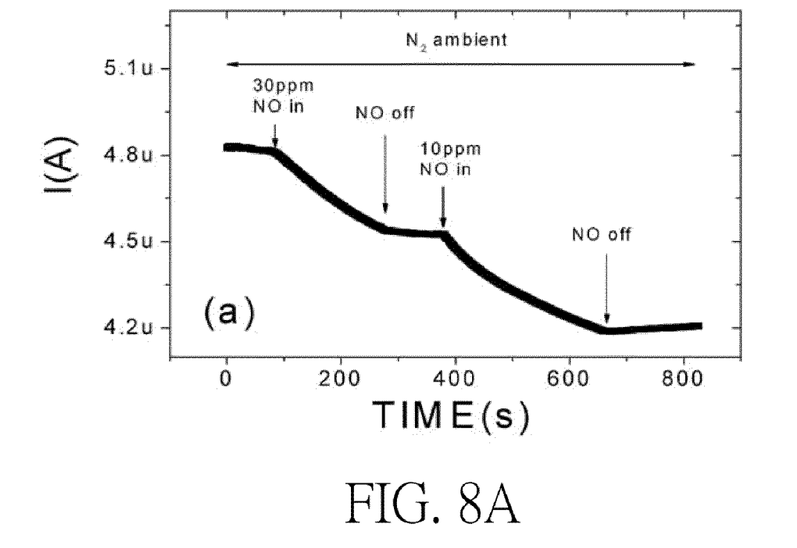
FIG. 8A shows variation in electric current of zinc oxide semiconductor device, which is not functionalized by hemin.

FIG. 8A shows the variation in the electric current of the un-functionalized zinc oxide semiconductor device. As shown in this figure, during the supply of the NO gas, there is no stable electric current generated by the un-functionalized zinc oxide semiconductor device. In addition, the variation in the electric current is irrelevant to the variation in NO concentration. Therefore, it is incapable of sensing the presence of ambient NO.

Figure 8B:
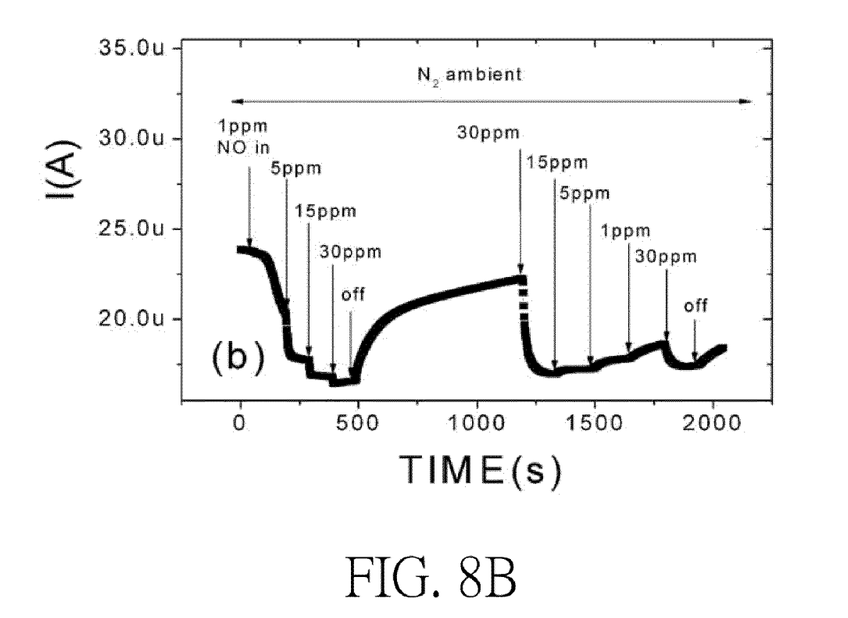
FIG. 8B shows variation in electric current of hemin-functionalized zinc oxide semiconductor device of the present invention.

FIG. 8B shows the variation in the electric current of the hemin-zinc oxide semiconductor device of the present invention. As shown in the figure, the variation in the electric current of the hemin-functionalized zinc oxide film is relevant to the variation in NO concentration, and the variation in the electric current is immediately sensitive to the variation in NO concentration. When the supply of NO gas is turned off, the electric current is increased. Thus, it is verified that this sensor device is reversible for the adsorption/desorption of the NO gas. Accordingly, the hemin-zinc oxide sensor device is actually adaptable for use as a nitric oxide sensor device.

Embodiment 4

The porous zinc oxide semiconductor device of the preparation example 1 (2) is functionalized by, for example, using the steps described in the preparation example 2 (1) so as to obtain the hemin-functionalized porous zinc oxide semiconductor sensor device (hereinafter abbreviated as hemin-porous zinc oxide sensor device).

Figure 9:
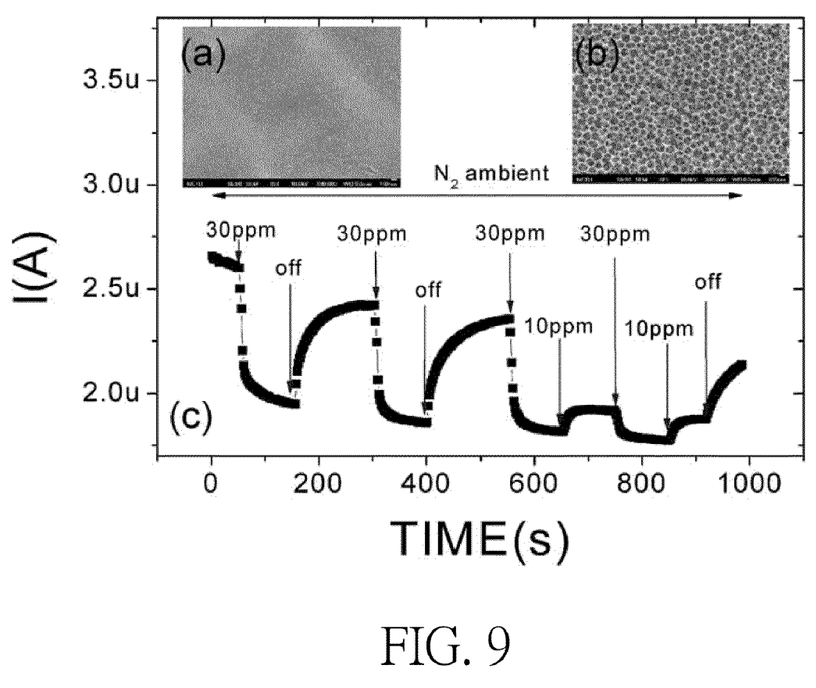
FIG. 9(a) and FIG. 9(b) are SEM diagrams showing the surfaces of zinc oxide and porous zinc oxide respectively.
FIG. 9(c) shows variation in electric current of hemin-porous zinc oxide sensor device.

FIG. 9(a) is a scanning electron microscope (SEM) diagram showing the surface of the comparison group, which is non-porous zinc oxide semiconductor. FIG. 9(b) is a SEM diagram showing the surface of the porous zinc oxide semiconductor. It is obvious from comparison between FIG. 9(a) and FIG. 9(b), the porous zinc oxide provides larger surface for functionalization by hemin.

Thereafter, the hemin-porous zinc oxide sensor device is disposed into the environment fulfilled with nitrogen gas and applied with a voltage. Then, the NO gas is supplied into the environment that is fulfilled with nitrogen gas. In addition, the variations in the electric currents of the sensor device when the concentration of NO gas is adjusted and when the supply of NO gas is turned on and turned off are shown in FIG. 9(c). FIG. 9(c) shows that the hemin-porous zinc oxide sensor device can rapidly, repeatedly response the real-time variation in the NO concentration by the variation in the electric current. When the supply of NO gas is turned off, the increasing speed of the electric current of the porous zinc oxide is faster than that of the non-porous zinc oxide. It is verified that the hemin-porous zinc oxide sensor device can increase the stability and sensitivity in detection of NO gas.

Embodiment 5

The hemin-porous zinc oxide sensor device of embodiment 4 is disposed into the environment fulfilled with nitrogen gas, and applied with a voltage. Thereafter, the NO gas is supplied into the environment that is fulfilled with nitrogen gas. In addition, the variations in the electric currents of the sensor device when the concentration of NO gas is adjusted and when the supply of NO gas is turned on and turned off and when different gases including oxygen ($O_2$) and carbon dioxide ($CO_2$) are supplied are shown in FIG. 10.

Figure 10:
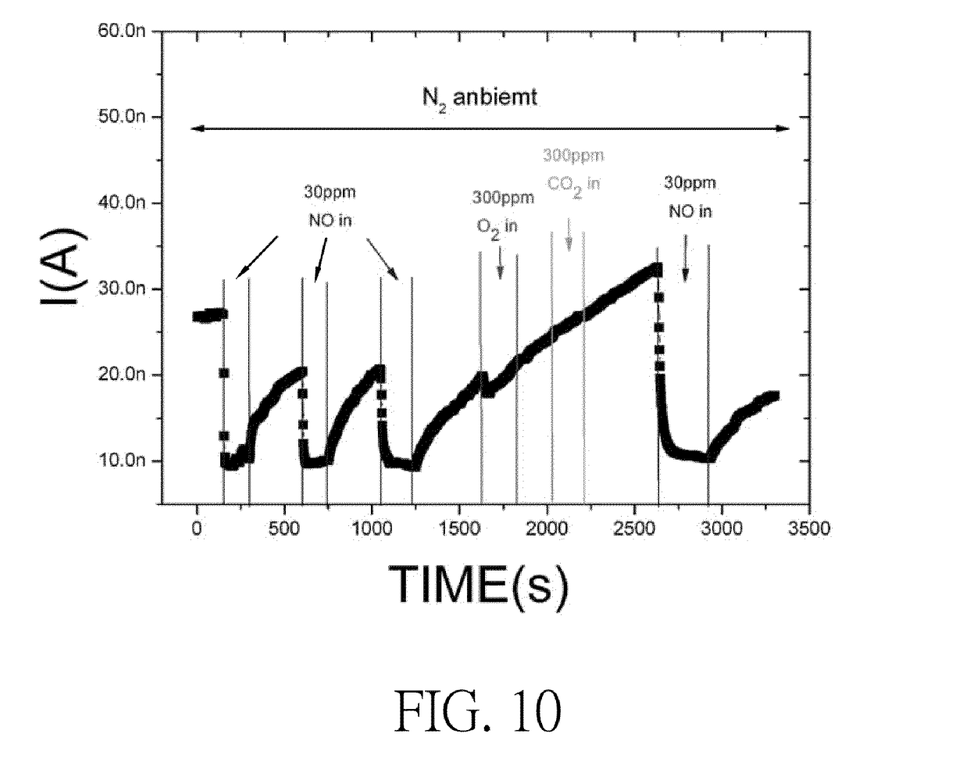
FIG. 10 shows variation in electric current of hemin-porous zinc oxide sensor device for various gases.

FIG. 10 shows that when 30 ppm of NO gas is supplied, the sensor device generates obvious variation in electric current. However, when 300 ppm of $O_2$ gas or 300 ppm of $CO_2$ gas is supplied, the sensor device does not generate corresponding variation in electric current. It is therefore verified that the sensor device of the present invention actually has outstanding selectivity in detected object.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A label-free sensor, comprising:
a substrate;
a first electrode formed on the substrate;
a second electrode formed on the substrate and spaced away from the first electrode; and
a semiconductor layer formed on the substrate and in contact with the first and second electrodes, wherein the semiconductor layer has a plurality of probe groups, which are bonded to the semiconductor layer by functionalization, for sensing a substance having bonding specificity with the probe groups, and wherein the first electrode and the second electrode are formed on the semiconductor layer such that the semiconductor layer is sandwiched between the substrate and the first and second electrodes.

2. The label-free sensor according to claim 1, wherein the probe groups are one or more chemical groups selected from the group consisting of —OH, —CHO, —COOH, —SO$_3$H, —CN, —NH$_2$, —SH, —COSH, —COOR, and halide.

3. The label-free sensor according to claim 1, wherein partial portion of the semiconductor layer is formed on the first electrode and the second electrode such that the first and second electrodes are sandwiched between the substrate and the semiconductor layer.

4. The label-free sensor according to claim 1, wherein semiconductor layer is of a metal oxide.

5. The label-free sensor according to claim 4, wherein the metal oxide is selected from the group consisting of zinc oxide, titanium oxide, indium oxide, and a combination thereof.

6. The label-free sensor according to claim 4, wherein the metal oxide has a porous configuration.

7. The label-free sensor according to claim 1, wherein the semiconductor layer is of an organic polymer semiconductor.

8. The label-free sensor according to claim 1, wherein the probe groups are one or more biomolecules selected from the group consisting of nucleic acid, antibody, carbohydrate, protein, amino acid, and enzyme.

9. The label-free sensor according to claim 7, wherein the organic polymer semiconductor has a porous configuration.

10. The label-free sensor according to claim 9, wherein the porous configuration is formed by stacking the organic polymer semiconductor in the form of silk.

11. The label-free sensor according to claim 3, wherein the probe groups are one or more biomolecules selected from the group consisting of nucleic acid, antibody, carbohydrate, protein, amino acid, and enzyme.

12. The label-free sensor according to claim 3, wherein the probe groups are one or more chemical groups selected from the group consisting of —OH, —CHO, —COOH, —SO$_3$H, —CN, —NH$_2$, —SH, —COSH, —COOR, and halide.

13. The label-free sensor according to claim 3, wherein the second electrode is spaced away from the first electrode by the semiconductor layer.

14. A sensing method, comprising:
applying a bias voltage to the first electrode and the second electrode of the label-free sensor according to claim 1 for generating an electric current;
contacting a detected object with the probe groups bonded to the semiconductor layer of the label-free sensor; and
measuring a variation in the electric current generated by the label-free sensor so as to determine whether a coupling-specific substance exists in the detected object.

15. The sensing method according to claim 14, wherein the detected object is in contact with the label-free sensor in a liquid.

16. The sensing method according to claim 14, wherein the detected object is a gaseous or gas-generating object.

17. A sensing system, comprising:
the label-free sensor according to claim 1;
a voltage supply device electrically connected to the first and second electrodes of the label-free sensor for applying a bias voltage to the sensor; and
an electricity measuring device electrically connected to the label-free sensor for measuring a variation in electricity.

18. The sensing system according to claim 14, wherein the variation in electricity is a variation in an electric current.

* * * * *